United States Patent [19]

van der Weerdt et al.

[11] 4,404,127

[45] Sep. 13, 1983

[54] PERFUME COMPOSITIONS AND PERFUMED MATERIALS AND ARTICLES, CONTAINING PHENYL-TETRAHYDROFURANS AS A FRAGRANCE

[75] Inventors: Antonius J. A. van der Weerdt, Huizen; Roeland Plomp, Almere-Haven; Willem Apeldoorn, Blaricum, all of Netherlands

[73] Assignee: Naarden International N.V., Naarden-Bussum, Netherlands

[21] Appl. No.: 307,613

[22] Filed: Oct. 1, 1981

[30] Foreign Application Priority Data

Oct. 6, 1980 [NL] Netherlands .................... 8005518

[51] Int. Cl.³ .................. A61K 7/46; C11B 9/00; C11D 17/00
[52] U.S. Cl. .................. 252/522 R; 252/522 A; 252/174.11; 424/65; 424/69; 424/70; 549/429
[58] Field of Search .......... 252/522 R, 522 A, 174.11; 549/429; 424/65, 69, 70

[56] References Cited

U.S. PATENT DOCUMENTS 4,115,406 9/1978 Vinals et al. ................... 252/522 R

FOREIGN PATENT DOCUMENTS 7807381 7/1978 Netherlands .

OTHER PUBLICATIONS

Yu, K. Yur'ev et al., 29 Zhur. Obschei. Khim., 3867–3872 (1959).
Kirrmann et al., Chemical Abstracts, 54:24619f.
L. Wartski, Bull. Soc. Chim., 3066–3076 (1965).
E. Compaigne et al., Journal of Organic Chemistry, vol. 32, 2372–2375 (1967).
N. I. Shuikin et al., Chemical Abstracts 64:3053d.
Ranfaing et al., Bull. Soc. Chim., 1048–1052 (1974).
S. Arctander, Perfume and Flavor Chemicals 169, Monograph 917 and 2602.
G. Camponovo et al., Chemical Abstracts 53:21175a.
N. Toshikazu et al., Chemical Abstracts 83:131400s.

*Primary Examiner*—John F. Niebling
*Attorney, Agent, or Firm*—Brumbaugh, Graves, Donohue & Raymond

[57] ABSTRACT

Perfume compositions, perfumed materials and articles containing one or more phenyl-tetrahydrofurans.

Use of one or more phenyl-tetrahydrofurans having formula 1 or 2 of the formula sheet in which $R_1$, $R_2$ and $R_3$ each represent a hydrogen atom or an alkyl group having 1 to 3 carbon atoms and $R_4$ represents a hydrogen atom, a methyl- or ethyl group as a perfume component in perfume compositions and in imparting perfume notes to materials and articles for example soaps, cleaning agents and cosmetic preparations.

7 Claims, 2 Drawing Figures

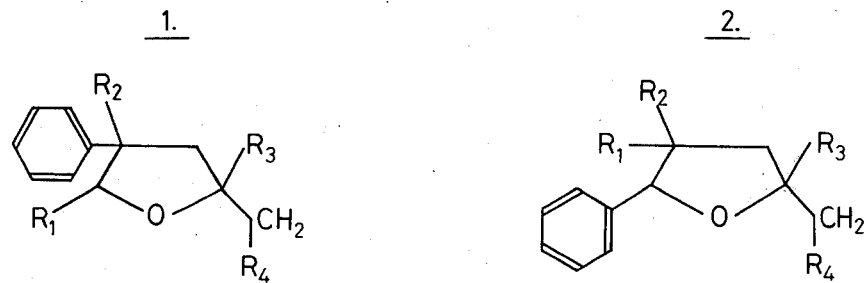
fig. 1
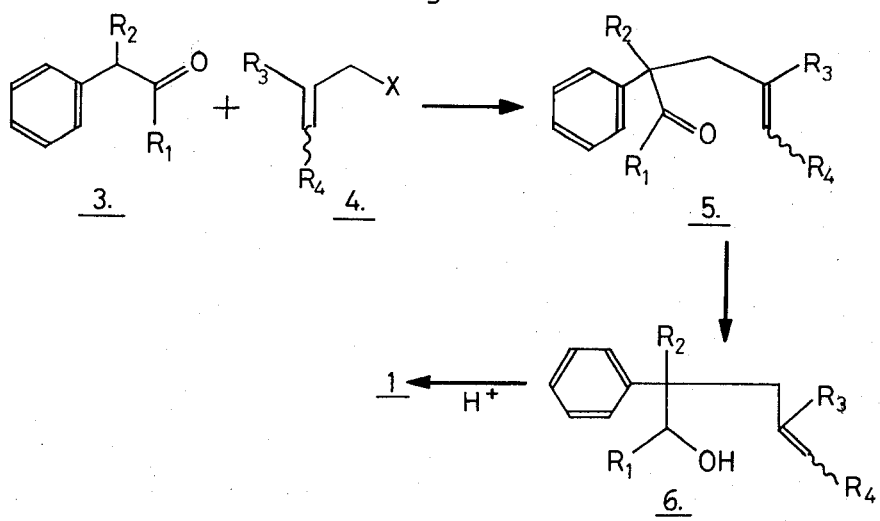
fig. 2
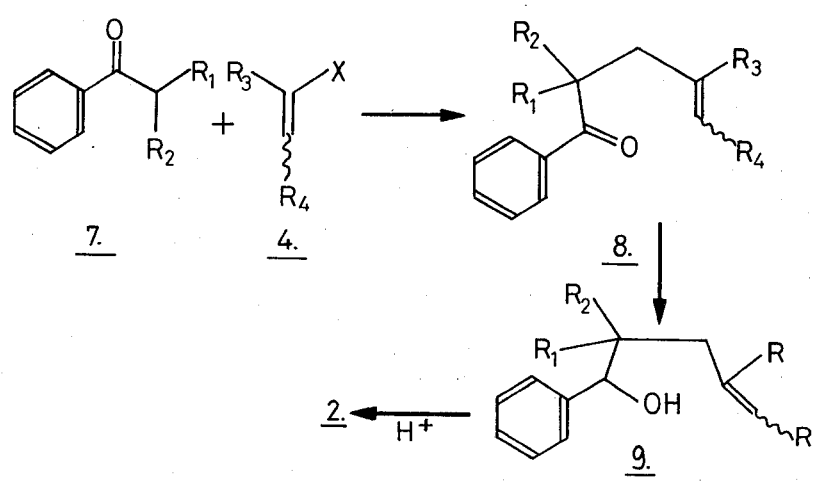

PERFUME COMPOSITIONS AND PERFUMED MATERIALS AND ARTICLES, CONTAINING PHENYL-TETRAHYDROFURANS AS A FRAGRANCE

The invention relates to perfume compositions containing substituted tetrahydrofurans as perfume base and to materials and articles perfumed with these compounds. The invention also relates to new phenyl-tetrahydrofurans.

There is a continuous interest for the preparation and application of synthetic fragrances because these fragrances can always be prepared in the quantity desired and with uniform quality, this contrary to naturally occurring substances. The modern detergents and cleaning agents to do require such high demands to the chemical stability of the perfume compositions used therein that many of the known synthetic fragrances do not come up to these requirements.

Therefore there is a special need for synthetic fragrances having a natural odor character as well as a great stability in aggressive, for instance strongly oxidative mediums.

The use of phenyl-tetrahydrofurans as a fragrance is not known. Of 2.5-diethyltetrahydrofuran and 2-(3-phenylpropyl)-tetrahydrofuran only the use in aroma compositions is known (S. Arctander, Perfume and Flavor Chemicals 1969, Monograph 917 and 2602). Of 3-phenylfuran it is only known that it is present in extracts of cocoa, malt, peanuts and tobacco; however, the organoleptycal properties are not described.

It was found that phenyl-tetrahydrofurans having the structure according to formula 1 or formula 2 on the formula sheet, in which $R_1$, $R_2$ and $R_3$ are hydrogen atoms or alkyl groups having 1 to 3 carbon atoms and $R_4$ is a hydrogen atom, a methyl or ethyl group, are valuable fragrances which may fulfill the above mentioned need.

The compounds 1a, b and c as stated below and belonging to the group of compounds having formula 1 and 2a belonging to the group having formula 2 are known per se and are described in the literature given therewith. For that reason no exclusive rights are claimed for the compounds as such. However, of these known compounds no olfactory properties are known.

1a: 2-Methyl-4-phenyl-tetrahydrofuran G. Camponovo et al., Arch. sci. (Geneva) 11,Spec. no. 203–8 (1958); vide C.A. 53 21175a.

1b: 2,2-dimethyl-4-phenyl-tetrahydrofuran N. Toshikazu et al., Yakugaku Zasshi 95 (no. 6), 710–14 (1975); vide C.A. 83 131400 s.

1c: 2,5-dimethyl-3-phenyl-tetrahydrofuran Yu. K. Yur'ev et al., Zhur. Obshchei. Khim. 29, 3867–72 (1959); vide C.A. 54 21033i.

2a: 2-methyl-5-phenyl-tetrahydrofuran A. Kirrmann and L. Wartski, Compt. Rend. 250, 3492–4 (1960); vide C.A. 54 24619 f and L. Wartski, Bull. Soc. Chim. France 1965, 3066–76; vide C.A. 64 1946c.

The other compounds having formula 1 or 2 are new.

The compounds according to the invention can be prepared according to methods known per se for analogical compounds for instance as described for compound 2a and related compounds by L. Wartski in Bull. Soc. Chim. France 1965, 3066 and 3077.

BRIEF DESCRIPTION OF THE DRAWINGS

Other preparation schemes are represented by FIG. 1 and FIG. 2, in which $R_1$ up to and including $R_4$ do have the meanings mentioned above.

The first step in both schemes represent the reaction of the phenyl substituted carbonyl compound having the formulas 3 respectively 7 with an allylic halide having formula 4, in which X is a chloro or bromo atom. According to a usual process the carbonyl compound can be reacted at first into a suitable enamine. However, one can also react the halide having formula 4 directly with the carbonyl compound under the influence of a base like NaOH and using therewith preferably a so called "phase-transfer-catalyse" under the influence of a suitable catalyst like a tetraalkyl ammonium halide. The alkenylated carbonyl compound having the formulas 5 respectively 8 is then reduced to the corresponding alcohol having the formulas 6 respectively 9. For this reduction process every method is suitable which does not affect the double bond. Very suitable are for instance reductions carried out with complex metal hydrides like $NaBH_4$ or a reduction according to Meerwein-Ponndorf-Verley. Finally the alcohol obtained in this way is cyclisized under the influence of an acidic catalyst like a small quantity of a strong anorganic or organic acid or an acidic ion-exchanger.

The compounds according to the invention can be used successfully in perfume compositions and for the perfumation of products for imparting thereto a bloomy, fruity, green or woody odor notes. The compounds according to the invention are characterized by a very natural odor character. Because of their great chemical stability these compounds are very suitable for perfuming of aggressive materials like detergents and cleaning agents.

Because especially the compounds having formula 1, in which $R_1$ up to $R_4$ represent a hydrogen atom or a methyl group, do have the best fresh and natural odor character these compounds are used preferably as fragrances.

The phrase "perfume composition" is used to mean a mixture of fragrances and optionally auxiliary substances that may be dissolved in an appropriate solvent or mixed with a powdery substrate used to impart a desired odor to the skin and/or various products. Examples of said products are: soaps, washing agents, dish washing and cleaning agents, air refreshers and room sprays, pommanders, candles, cosmetics such as creams, colognes, pre- and after-shaving lotions, talcum powders, hair care agents, body deodorants and antiperspirants.

Fragrances and mixtures thereof which can be used for the preparation of perfume compositions are e.g. naturally occurring products such as essential oils, absolutes, resinoids, resins, concretes a.s.o., but also synthetic fragrances, such as hydrocarbons, alcohols, aldehydes, ketones, ethers, acids, esters, acetals, ketals, nitrils a.s.o., covering saturated and unsaturated compounds, aliphatic, carbocyclic and heterocyclic compounds.

Examples of fragrances to be used in combination with the compounds according to the invention are: geraniol, geranyl acetate, linalool, linalyl acetate, tetrahydrolinalool, citronellol, citronellyl acetate, myrcenol, myrcenyl acetate, dihydro myrcenol, dihydro myrcenyl acetate, tetrahydro myrcenol, terpineol, terpinyl acetate, nopol, nopyl acetate, β-phenyl ethanol, β-phenylethyl acetate, benzyl alcohol, benzyl acetate, benzyl salicylate, benzyl benzoate, amyl salicylate. styrallyl acetate, dimethylbenzyl carbinol, trichloro methylphenylcarbinyl acetate, p-tert.butyl cyclohexyl acetate, isononyl acetate, vetiveryl acetate, vetiverol, α-hexyl cinnamon aldehyde, 2-methyl-3-(p-tert.butyl-phenyl)-propanol, 2-methyl-3-(p-isopropyl phenyl)-propanol, 3-(p-tert.butyl-phenyl)-propanol, tricyclodecenyl acetate, tricyclodecenyl propionate, 4-(4-hydroxy-4-methylpentyl)-3-cyclohexene carbaldehyde, 4-(4-methyl--3-pentenyl)-3-cyclohexene carbaldehyde, 4-acetoxy-3-pentyl-tetrahydropyran, 3-carboxymethyl-2-pentylcyclopentane, 2-n-heptyl cyclopentanone, 3-methyl-2-pentyl-2-cyclopentanone, n-decanal, n-dodecanal, 9-decenol-1, phenoxyethyl isobutyrate, phenyl acetaldehyde dimethylacetal, phenyl acetaldehyde diethylacetal, geranyl nitril, citronellyl nitril, cedryl acetate, 3-isocamphyl cyclohexanol, cedrylmethylether, isolongifolanon, aubepine nitrile, aubepine, heliotropine, coumarine, eugenol, vanilline, diphenyl oxide, hydroxy citronellal, ionones, methyl ionones, isomethyl ionones, irones, cis-3-hexenol and esters thereof, indan mush fragrances, tetraline musk fragrances, isochroman musk fragrances, macrocyclic ketones, macrolactone musk fragrances, ethylene brassylate, aromatic nitromusk fragrances.

Auxiliary agents and solvents that may be incorporated into perfume compositions according to the invention are e.g. ethanol, isopropanol, diethyleneglycol monoethylether, diethyl phtalate a.s.o.

The amount of tetrahydrofurans according to the invention that can be used in a perfume composition or in a perfumed product can be varied within broad limits and depends e.g. on the product wherein the perfume is used, the nature and the amount of the further components of the perfume compositions and the odor effect desired. Therefore, it is only possible to indicate very rough limits, which give, however, a person skilled in the art sufficient information for using the compounds according to the invention by himself. In most cases a quantity of only 0.01% in a perfume composition is sufficient to obtain a clearly observable odor effect. On the other side it is possible to use a quantity of 30% or even more in a composition for achieving specific odor effects.

In products perfumed with the aid of perfume compositions according to the invention the concentration is lower and depends on the quantity of the composition used in the product.

The following examples only illustrate the preparation and the use of the compounds according to the invention and do not restrict the invention thereto.

EXAMPLE I 2.4-Dimethyl-4-phenyl-tetrahydrofuran (a) A mixture of 130 g toluene, 92 g (1.2 mole) allylchloride, 120 g 50-percents sodium lye (1.5 mole) and 3 g tricaprylmethylammoniumchloride is heated to 40° C. under a nitrogen atmosphere. Then under agitation 134 g (1 mole) hydratropic aldehyde (2-phenyl-propanal) is added in 30 minutes and the temperature rose to 80° C. The reaction mixture was kept another hour on this temperature under agitation. After cooling to room temperature the reaction mixture was agitated 10 minutes with 150 g water. The layers were separated and the organic layer was washed one time with a saturated sodium-chloride solution. The organic layer was evaporated and the unreacted hydratropic aldehyde was subsequently distilled in vacuo.

Yield: 167 g raw 2-allyl-2-phenyl-propanal.

(b) The quantity of aldehyde obtained according to (a) was mixed with 148 g sec. butanol and 12 g aluminum-sec.butylate and heated to reflux temperature. Then about 90 g methylethylketone was distilled. After the reaction mixture was cooled to room temperature the mixture was added under agitation to 100 g 10-percents hydrochloric acid and thereupon extracted with 100 g toluene. The organic layer was separated and washed with subsequently 50 ml water, 50 ml 10-percents soda solution and 50 ml saturated sodiumchloride solution. The organic layer was evaporated and the residue was distilled in vacuo in a vigreux. Yield: 148 g 2-allyl-2-phenyl-propanol-1 (contents: 94%; boiling point: 100°–115° C./0.5 kPa; yield in stage (a) and (b): 80%.

(c) The obtained quantity of alcohol was cyclisized by adding 3 g Amberlyst 15 (an acidic ion-exchanger manufactured by Röhm & Haas) as a catalyst and refluxing the mixture 5 hours at a temperature of 155°–160° C. Then the catalyst was filtrated and the filtrate was distilled in vacuo. The destillate was further fractionated in a 2 m vigreux whereby 96 g 2.4-dimethyl-4-phenyl-tetrahydrofuran was obtained. Boiling point: 76°–78° C./0.1 kPa; $n_D^{20}$=1.5178. Yield (stage c): 69%. The compound has a very intensive fruity and somewhat bloomy odor strongly remembering to rhubarb and grape fruit.

EXAMPLE II 2.2.4-trimethyl-4-phenyl-tetrahydrofuran (a) Using 46 g metallylchloride and 60 g hydratropic aldehyde as starting compounds 2.4-dimethyl-2-phenyl-4-pentenal was prepared according to the method described in example (Ia). Yield: 65 g.

(b) 60 g Of the obtained aldehyde was added in 30 minutes under agitation to a solution of 10 g NaBH₄ in 200 ml ethanol and 10 ml water, whereby the temperature of the reaction mixture rose to 60° C. The mixture was agitated another hour. Then 50 ml water was added and the mixture was extracted with ether. The extract was washed with water and evaporated. The residue was distilled in vacuo.

Yield: 56 g 2.4-dimethyl-2-phenyl-4-pentenol-1;

Boiling point: 100°–110° C./0.5 kPa; Yield (in stage a and b): 71%.

(c) 50 g Of the obtained alcohol was taken up in 200 ml toluene and after that 2 g Amberlyst 15 was added. The mixture was refluxed 3 hours. After cooling the reaction mixture was filtrated and the filtrate evaporated. The residu was fractionated in vacuo.

Yield: 40 g (80%) 2.2.4-trimethyl-4-phenyltetrahydrofuran;

Boiling point: 95° C./0.2 kPa; $n_D^{20}$=1.5101.

The compound has a pleasant bloomy and honeylike odor.

EXAMPLE III 3.3.5-trimethyl-2-phenyl-tetrahydrofuran (a) Using 90 g allylchloride and 120 g isopropyl-phenylketone as starting compounds 2.2-dimethyl-1-phenyl-4-pentenon-1 was prepared according to the method described in example (Ia). Yield: 32 g. 54 g Isopropyl-phenylketone could be won back.

(b) 30 g Of the obtained ketone was reduced with 10 g NaBH$_4$ in 200 ml ethanol and 10 ml water according to the method described in example (II b). Yield: 25 g 2.2-dimethyl-1-phenyl-4-pentenol-1.

(c) A mixture of 20 g of this alcohol and 2 g p.toluenesulphonic acid was heated 20 minutes at a temperature of about 180° C. Then the mixture was distilled in vacuo whereby 16 g of a mixture was obtained containing 70% 3.3.5-trimethyl-2-phenyl-tetrahydrofuran; boiling point 80° C./0.1 kPa. The wanted compound could be isolated from this mixture by means of G.L.C. (Gas-Liquid-Chromatography) (column: 2 m, ¼", 10% OV 17); n$_D^{20}$=1.5120. The mixture obtained by distillation as well as the pure compound do have a strong woody odor having a bloomy, to roses remembering note.

EXAMPLE IV

2-Ethyl-4-phenyl-4-methyl-tetrahydrofuran (a) A mixture of 70 g hydratropic aldehyde and 70 g crotylchloride was added under agitation in 1 hour to a mixture of 60 ml 50-percents sodium lye, 100 ml toluene and 1 g tricapryl-methylammoniumchloride. The temperature rose thereby to 60° C. The mixture was stirred another hour and poured in 150 ml water. The organic layer was separated and washed with water and with a sodiumchloride solution (saturated). The toluene solution was evaporated and the residue was distilled in vacuo. Yield: 83 g 2-phenyl-2-methyl-4-hexenal.

(b) 75 g Of this aldehyde was reduced to the corresponding alcohol by means of 10 g NaBH$_4$, as described in example (II b). Yield: 68 g 2-phenyl-2-methyl-4-hexenol-1.

(c) 63 g Of this Alcohol and 5 g Amberlyst 15 in 100 ml toluene were heated 3 hours at a temperature of 110° C. After cooling the catalyst was filtrated and the solution evaporated. The residue was distilled in a vacuo. By means of this stage 49 g of an about 1:1 mixture of 2-ethyl-4-phenyl-4-methyltetrahydrofuran and 2.5-dimethyl-5-phenyltetrahydropyran was obtained: boiling point 90°-95° C./0.3 kPa; n$_D^{20}$=1.5321. The mixture has a somewhat green but especially an intensive fruity, to rhubarb and grape fruit remembering odor with a weak chocolatelike note.

The 2-ethyl-4-phenyl-methyltetrahydrofuran was isolated by means of G.L.C. (column: 2m, ¼", 10% DEGS). The odor of this compound was very much alike the odor of the mixture but missed the chocolatelike note.

For the preparation of perfume compositions the mixture was as well as usable as the isolated compound.

EXAMPLE V 2.5-Dimethyl-3-phenyl-tetrahydrofuran (a) Using 38 g (0.5 mole) allylchloride and 100 g (0.75 mole) benzylmethylketone in 100 ml 50-percents lye, 100 ml toluene and 3 g tricapryl-methyl-ammoniumchloride as starting mixture 3-phenyl-5-hexenon-2 was obtained according to the method described in example (IV a). Yield: 28 g (content 90%); boiling point 95°-100° C./0.4 kPa.

(b) 20 g Of the obtained ketone was reduced by means of NaBH$_4$ to the corresponding alcohol according to the method described in example (II b). Yield: 16 g 3-phenyl-5-hexenol-2.

(c) 14 g Of this alcohol and 1 g Amberlyst 15 in 100 ml toluene were heated 2 hours at a temperature of 110° C. After cooling the catalyst was filtrated, the solvent evaporated and the residue distilled in vacuo. Yield: 7 g 2.5-dimethyl-3-phenyltetrahydrofuran; boiling point 98° C./0.2 kPa; n$_D^{20}$=1.5171. The compound has an intensive green and somewhat citruslike odor.

EXAMPLE VI

A perfume composition of the "bouquet" type was prepared according to the following receipt:

|  | parts by weight |
|---|---|
| Bergamotoil, free of bergaptene | 150 |
| α-Isomethyljonon | 130 |
| Geraniol | 85 |
| Hydroxycitronellal | 75 |
| Vetiverylacetate | 70 |
| Benzylacetate | 70 |
| Jasmin NB 133[1] | 50 |
| Ylang-Ylangoil | 50 |
| Geraniumoil Bourbon | 50 |
| Rosana NB 131[1] | 50 |
| Musk-ketone | 30 |
| Coumarin | 30 |
| Sandelwood-oil, East Indian | 30 |
| Benzoëresinoid Siam | 25 |
| Palmarosaoil | 25 |
| Oil of citron, Italian | 20 |
| Mousse-de-chene-absolue | 15 |
| Musk R$_1$[1] | 10 |
| Heliotropine | 10 |
| Styrax resinoide | 5 |
| Undecen-10-al | 5 |
| Decanal | 5 |
| 2.4-dimethyl-4-phenyl-tetrahydrofuran | 10[2] |
|  | 1000 |

[1]Fragrances and perfume bases put upon the market by Naarden International N.V.
[2]This component could succesfully be replaced by 20 parts by weight of 2-ethyl-4-phenyl-4-methyltetrahydrofuran obtained according to example IV.

EXAMPLE VII

A perfumed toiletsoap was prepared by thoroughly mixing of 1 kg white soap grains, 10 g of the above mentioned perfume composition and 10 g soap-dye in a pilling machine. By this process perfumed coloured flakes of soap were obtained, which were pressed in the usual way to pieces of toilet soap. The pieces of toilet soap obtained according to the above had a pleasant and stable odor.

EXAMPLE VIII

A perfume composition for an after-shave-lotion was prepared according to the following receipt:

|  | parts by weight |
|---|---|
| Bergamotoil, free of bergaptene | 375 |
| Oil of citron, Italian | 200 |
| Vetiverylacetate | 50 |
| α-n-Amylcinnamic aldehyde | 50 |
| 4-Acetoxy-3-pentyltetrahydropyran | 50 |
| Lavande concrete | 50 |
| α-Isomethyljonon | 50 |
| Jasmin NB 133[1] | 30 |
| Acetylcedrene | 30 |
| Sandelwoodoil, East-Indian | 30 |
| Hydroxycitronellal | 30 |
| Oil of Cypresses | 30 |
| Musk R$_1$[1] | 10 |
| Mousse d'arbre absolue | 10 |
| 2.5-dimethyl-3-phenyl-tetrahydrofuran | 5 |
|  | 1000 |

[1]Fragrances and prefume bases put upon the market by Naarden International N.V.

EXAMPLE IX

An after-shave-lotion perfumed with a composition according to example VIII was prepared according to the following receipt:

|   |   | parts by weight |
|---|---|---|
| (A) | l-Menthol | 0.3 |
|   | Uvinol D 50[1] | 0.5 |
|   | Propyleneglycol | 30.0 |
|   | Ethanol | 535.0 |
| (B) | Aluminum-chlorohydrate-allantoinate | 2.0 |
|   | Lactic acid | 2.0 |
|   | Water (distilled) | 400.2 |
| (C) | Perfume (vide above) | 20.0 |
|   | Cremophor RH40[2] | 10.0 |
|   |   | 1000.0 |

[1]trade mark of BASF for 2.2′,4.4′-tetrahydroxybenzofenon.

[2]trade mark of BASF for a reaction product of hydrogenated castor oil and ethyleneoxide.

The components mentioned under (A), (B) and (C) were mixed separately to the mixtures A, B and C. Mixture B was then added under good agitation to mixture. A. After that mixture C was added and the obtained mixture was agitated homogeneously. In this way a somewhat astringating and pleasantly smelling after-shave-lotion was obtained.

We claim:

1. Compounds having the formula

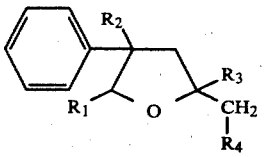

wherein $R_1$, $R_2$ and $R_3$ are selected from the group consisting of H and an alkyl group having 1–3 carbon atoms and $R_4$ is selected from the group consisting of H, $CH_3$ and $C_2H_5$, providing that $R_1$, $R_2$, $R_3$ and $R_4$ are not each H and further providing that when $R_2$ and $R_4$ are H, one of $R_1$ and $R_3$ is not H and the other a methyl group.

2. Compounds having the formula

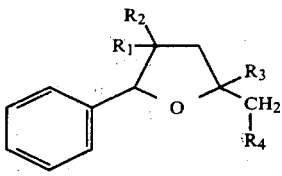

wherein $R_1$, $R_2$ and $R_3$ are selected from a group consisting of H and an alkyl group having 1–3 carbon atoms and $R_4$ is selected from the group consisting of H, $CH_3$ and $C_2H_5$, providing that $R_1$, $R_2$, $R_3$ and $R_4$ are not each H and when $R_4$ is $C_2H_5$, $R_1$, $R_2$ and $R_3$ are not each H.

3. Perfume compositions comprising at least one compound having the formula

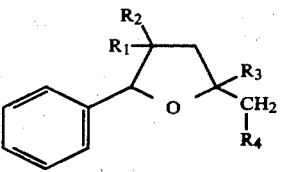

wherein, $R_1$, $R_2$ and $R_3$ are selected from the group consisting of H and an alkyl group having 1–3 carbon atoms and $R_4$ is selected from the group consisting of H, $CH_3$ and $C_2H_5$.

4. Perfume compositions comprising at least one compound having the formula wherein $R_1$, $R_2$ and $R_3$ are selected from a group consisting of H and an alkyl group having 1–3 carbon atoms and $R_4$ is selected from the group consisting of H, $CH_3$ and $C_2H_5$.

5. Perfume compositions according to claim 3 comprising 0.01–30% by weight of at least one of the compounds of claim 3.

6. Perfume compositions according to claim 4 comprising 0.01–30% by weight of at least one of the compounds of claim 4.

7. Perfumed products comprising a carrier and at least one perfume composition of claim 3 or 4.

* * * * *